(12) United States Patent
Miyamoto

(10) Patent No.: US 8,798,352 B2
(45) Date of Patent: Aug. 5, 2014

(54) X-RAY RADIOSCOPY DEVICE, MOVING PICTURE PROCESSING METHOD, PROGRAM, AND STORAGE MEDIUM

(75) Inventor: Hideaki Miyamoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 829 days.

(21) Appl. No.: 12/431,206

(22) Filed: Apr. 28, 2009

(65) Prior Publication Data

US 2009/0279663 A1 Nov. 12, 2009

(30) Foreign Application Priority Data

May 7, 2008 (JP) ................................. 2008-121644

(51) Int. Cl.
*G06K 9/00* (2006.01)

(52) U.S. Cl.
USPC .......................................................... 382/132

(58) Field of Classification Search
USPC ....................................... 382/132; 378/62, 95
See application file for complete search history.

(56) References Cited

U.S. PATENT DOCUMENTS

| 7,489,799 | B2* | 2/2009 | Nilsen et al. ................... 382/100 |
| 7,680,307 | B2* | 3/2010 | Sathyanarayana ............. 382/128 |
| 2002/0018590 | A1* | 2/2002 | Shinbata ........................ 382/132 |
| 2005/0169534 | A1 | 8/2005 | Takahashi ....................... 382/203 |
| 2007/0269019 | A1* | 11/2007 | Spahn ............................ 378/207 |
| 2009/0175411 | A1* | 7/2009 | Gudmundson et al. ......... 378/57 |
| 2009/0257637 | A1* | 10/2009 | Bohm et al. ................... 382/132 |

FOREIGN PATENT DOCUMENTS

| JP | 2000-10840 | 1/2000 |
| JP | 2003-250789 | 9/2003 |
| JP | 2005-218581 | 8/2005 |

* cited by examiner

*Primary Examiner* — Jonathan Hansen
(74) *Attorney, Agent, or Firm* — Fitzpatrick, Cella, Harper & Scinto

(57) ABSTRACT

An X-ray radioscopy device comprises: an image capturing unit that captures a moving image of an object that has been irradiated by X-rays; an analysis processing unit that performs different analysis processes in parallel on each frame that makes up the moving image and extracts, from each frame, a region of interest defined as a portion of the object subject to radioscopy by the X-ray irradiation; and a selection unit that performs an evaluation operation on the multiple regions of interest extracted based on the different analysis processes, and based on the result of the evaluation operation, selects and outputs a single region of interest from the multiple regions of interest extracted by the analysis processing unit.

25 Claims, 13 Drawing Sheets

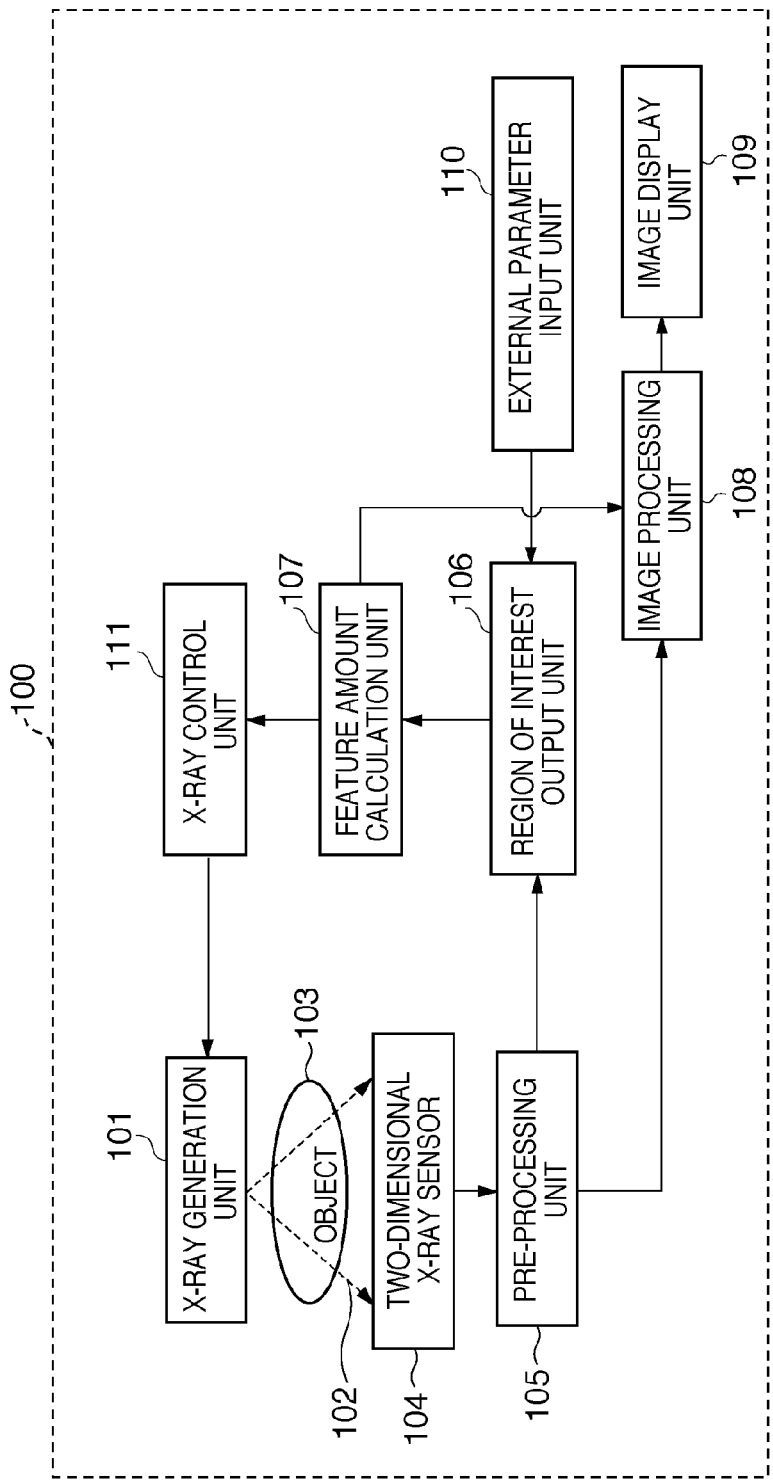

X-RAY RADIOSCOPY DEVICE, MOVING PICTURE PROCESSING METHOD, PROGRAM, AND STORAGE MEDIUM

BACKGROUND OF THE INVENTION

1. Field of the Invention

The present invention relates to an image processing technique based on radioscopy images obtained through moving picture imaging such as radioscopy imaging.

2. Description of the Related Art

Due to recent advancements in digital techniques, it has become common to perform digital processing on, for example, images obtained through medical X-ray radioscopy. Two-dimensional X-ray sensors capable of outputting X-ray images as digital data are being developed in place of X-ray imaging using conventional X-ray diagnostic film. Digital image processing, such as tone processing and the like, has become essential in X-ray radioscopy devices that use sensors such as the stated two-dimensional X-ray sensors.

Auto-exposure control (AEC), which detects the amount of X-rays that permeate an object and controls the X-ray amount so that it is neither too high nor too low, is carried out in X-ray radioscopy. In auto-exposure control, a feature amount, such as the average value of an X-ray radioscopy image obtained from X-rays having a pulse-shaped waveform irradiated from an X-ray generation unit 101, is obtained first. Then, the X-ray irradiation conditions (tube voltage, tube current, X-ray pulsewidth of the X-ray generation unit) are controlled based on a comparison between the level of the feature amount and a reference value, in order to achieve a desired exposure.

Image processing, auto-exposure control, and so on performed by an X-ray radioscopy imaging device aim to appropriately display a region of interest corresponding to an anatomical structure in a human body, which is the most important part of the image for diagnostic purposes.

In the image processing, auto-exposure control, and so on performed by an X-ray radioscopy imaging device, the region of interest is extracted from the captured image, and the feature amount used in the image processing, auto-exposure control, and so on is calculated from the extracted region of interest. The region of interest is different depending on the portion to be imaged, the purpose of the imaging, and so on. For example, when performing radioscopy of the stomach using a barium liquid, the stomach wall is taken as the region of interest in order to detect polyps present therein; when capturing moving pictures of the chest area, the lung field region is the region of interest; and in cardiac catheterization, the tip of the catheter and the surrounding region thereof is the region of interest.

Meanwhile, regions outside the exposure field when the exposure field is limited using a collimator, transparent regions where X-rays enter directly into the sensor without passing through the object, and so on are detrimental to the proper calculation of the feature amount and should therefore be left out of the region of interest. In addition, when regions in which the X-ray absorption rate differs greatly from that of the object, such as pieces of metal, are contained within the region of interest, such regions are also detrimental to the proper calculation of the feature amount and should therefore be left out of the region of interest.

Conventionally, setting a threshold for differentiating between a region of interest and other regions, and then performing a thresholding process for extracting the region of interest based on this threshold, an edge extraction process for extracting contour forms of an object based on the form of the gradation distribution of the image, or the like has been used as a method for extracting a region of interest from an image.

For example, Japanese Patent Laid-Open No. 2000-10840 discloses a method for creating a density histogram on the object regions within a radiation image and performing tone correction, dynamic ranging, and so on of the radiation image based on a feature amount of the image calculated from the density histogram. Stable extraction of the feature amount of the object region within the image can be performed by extracting image component information corresponding to the bones, soft tissues, and the like of the object using transparency elimination, the form of the histogram, and so on. Effective image processing is thus possible even in cases where, for example, the maximum pixel density values in the object region of the radiation image are less than a predetermined pixel density value.

Meanwhile, Japanese Patent Laid-Open No. 2005-218581 discloses a method for extracting an exposure field region in order to optimize the image processing parameters. In this method, scores are given regarding how closely a pixel of interest and a pattern of the surrounding pixels thereof resemble the border of the exposure field, and an exposure field candidate region is calculated so as to correspond to a collimator form, such as a circle or a polygon. A form feature amount, such as the degree of circularity, is found for the exposure field candidate region, and the form is identified thereby; the exposure field is then extracted using an exposure field recognition algorithm tailored to the identified shape. As the algorithm tailored to the identified shape, linear detection processing such as a Hough transform is employed for polygons, whereas template matching with circular forms or the like is employed for circles; this increases the accuracy.

Finally, in Japanese Patent Laid-Open No. 2003-250789, a region of interest is extracted to be used for feature amount calculation in order to perform either auto-exposure control, image density conversion, or both as appropriate in radioscopy that generates an image at the comparatively low rate of three to five frames a second. In this method, the image data of a quadrangular exposure field region is first projected (accumulated) in the top, bottom, right, and left directions of the image, after which a one-dimensional array is created for each direction; a secondary differentiation computation is then performed on these arrays. The positions having the maximum values are taken as the external tangents (borderlines) of the exposure field in each direction and cut out, extracting the exposure field; a process for extracting the region of interest is then performed on the obtained result of cutting out the exposure field. The process for extracting the region of interest is performed while switching the extraction algorithm for each region of interest based on information regarding the portion that has been imaged or order information. Algorithms that utilize analysis of image histograms, morphology computations, logical computation of binary images, and so on are disclosed as methods for setting a predetermined region, detecting the stomach wall as the peripheral contour region of a barium mass, and detecting the lung field region when capturing a moving picture of the chest area.

However, generally, algorithms for extracting a region of interest are complicated. In particular, in a device that processes a large amount of data, such as with X-ray radioscopy, it is difficult to extract a region of interest between the X-ray irradiation and the display with high accuracy and at the high frame rate (25 to 30 fps) that is required. The abovementioned conventional techniques are used for extracting a region of interest from an image obtained through still-image capturing or radioscopy at a comparatively low frame rate, and no consideration is given to a technique for extracting an appropriate region of interest from a moving image obtained through high-frame rate radioscopy.

SUMMARY OF THE INVENTION

Accordingly, the present invention provides an X-ray radioscopy device capable of extracting, in real time, a region of interest used in feature amount calculation, when capturing a moving picture at a high frame rate, particularly in X-ray radioscopy.

According to one aspect of the present invention, there is provided an X-ray radioscopy device comprising: an image capturing unit that captures a moving image of an object that has been irradiated by X-rays; an analysis processing unit that performs different analysis processes in parallel on each frame that makes up the moving image and extracts, from each frame, a region of interest defined as a portion of the object subject to radioscopy by the X-ray irradiation; and a selection unit that performs an evaluation operation on the multiple regions of interest extracted based on the different analysis processes, and based on the result of the evaluation operation, selects and outputs a single region of interest from the multiple regions of interest extracted by the analysis processing unit.

According to another aspect of the present invention, there is provided a moving image processing method for processing a moving image of an object that has been irradiated by X-rays, the method comprising: an analysis processing step of performing different analysis processes in parallel on each frame that makes up the moving image and extracting, from each frame, a region of interest defined as a portion of the object subject to radioscopy by the X-ray irradiation; and a selection step of performing an evaluation operation on the multiple regions of interest extracted based on the different analysis processes, and based on the result of the evaluation operation, selecting and outputting a single region of interest from the multiple regions of interest extracted in the analysis processing step.

According to the present invention, it is possible to extract, in real time, a region of interest for calculating a feature amount used in image processing, X-ray control, and so on in the capturing of a moving picture as exemplified by X-ray radioscopy.

Further features of the present invention will become apparent from the following description of exemplary embodiments with reference to the attached drawings.

BRIEF DESCRIPTION OF THE DRAWINGS

FIG. 1A is a diagram illustrating the configuration of an X-ray radioscopy device according to a first embodiment.

FIG. 7 is a diagram illustrating an example of a histogram created through processing performed by a first analysis processing unit 106a.

DESCRIPTION OF THE EMBODIMENTS

Figure 1B:
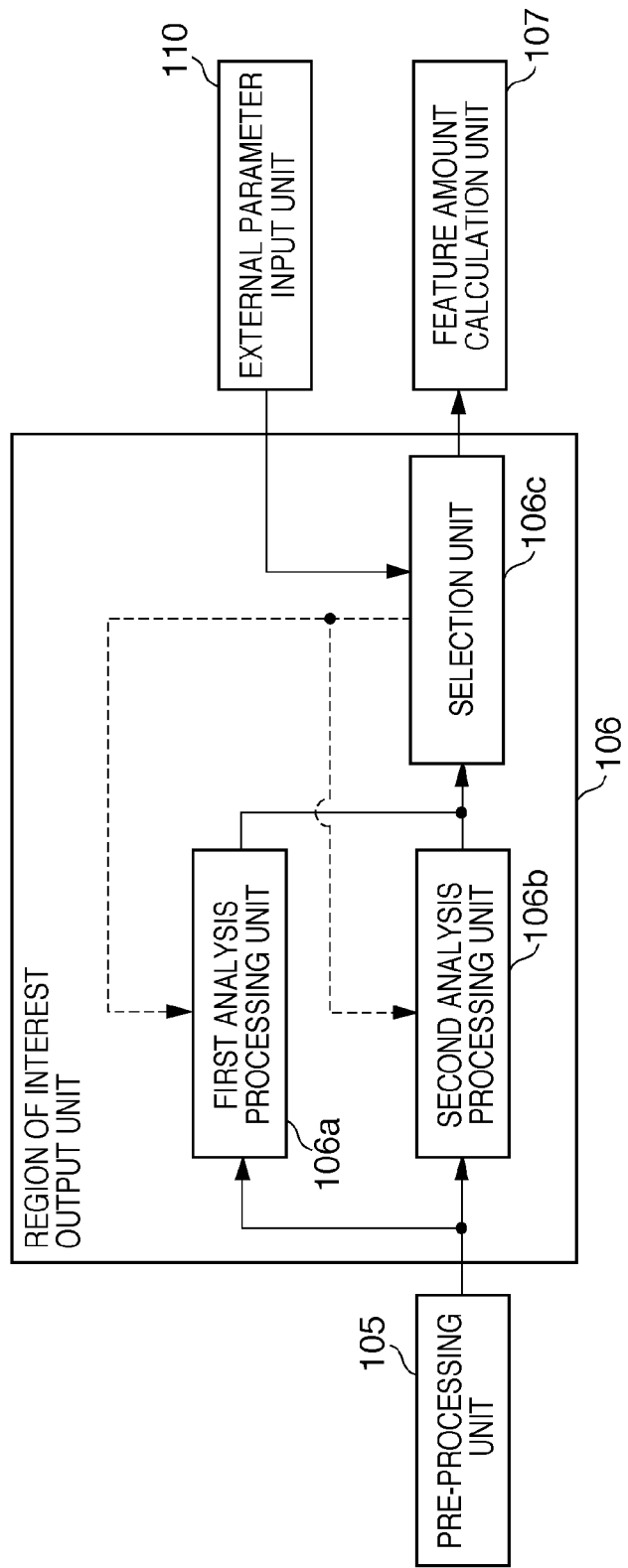
FIG. 1B is a diagram illustrating the specific configuration of a region of interest output unit.

Hereinafter, exemplary preferred embodiments of the present invention shall be described in detail with reference to the diagrams. However, it should be noted that the constituent elements denoted in the following embodiments are to be taken as examples only; the technical scope of the present invention is defined by the appended claims, and is not intended to be limited by the individual embodiments described hereinafter.

First Embodiment

An X-ray radioscopy device according to a first embodiment of the present invention shall be described with reference to FIG. 1A. An X-ray radioscopy device 100 includes an X-ray generation unit 101 capable of generating 3 to 30 X-ray pulses per second and a two-dimensional X-ray sensor 104 that receives X-rays 102 that have permeated an object 103 and captures a moving image synchronized with the X-ray pulses. The two-dimensional X-ray sensor 104 functions as an image capturing unit that captures a moving image of an object that has been irradiated with X-rays.

The X-ray radioscopy device 100 also includes a pre-processing unit 105 that performs pre-processing on each frame of the moving image outputted from the two-dimensional X-ray sensor 104 and a region of interest output unit 106 that extracts a region of interest from each frame of the moving image that has been pre-processed by the pre-processing unit 105. The region of interest output unit 106 is capable of extracting a region of interest from a frame to be processed using at least one of, for example, histogram analysis, edge detection through spatial filtering, a Hough transform, morphology computation, and pattern matching.

The X-ray radioscopy device 100 also includes a feature amount calculation unit 107 that calculates a feature amount based on the region of interest extracted by the region of interest output unit 106. The feature amount calculation unit 107 is capable of calculating, based on the extracted region of interest, a feature amount expressing, for example, at least one of the following: the position, size, form, average luminance value, maximum luminance value, minimum luminance value, central position, variance, and standard deviation of the region of interest.

Furthermore, the X-ray radioscopy device 100 also includes an image processing device (image processing unit 108) that performs image processing on each frame of the moving image on which pre-processing has been performed by the pre-processing unit 105, using the feature amount calculated by the feature amount calculation unit 107. The image processing unit 108 is capable of at least one of, for example, tone conversion processing, sharpening processing, noise suppressing processing, and region of interest cutout processing as the stated image processing, based on the feature amount.

The X-ray radioscopy device 100 further includes an image display unit 109 that displays the moving image on which the image processing has been performed by the image processing unit 108 as an X-ray radioscopy image.

The X-ray radioscopy device 100 also includes an external parameter input unit 110 that inputs various setting parameters to the region of interest output unit 106 from the exterior. Finally, the X-ray radioscopy device 100 includes an X-ray control unit 111 that controls the irradiation conditions for the next irradiation performed by the X-ray generation unit 101 based on the feature amount calculated by the feature amount calculation unit 107.

FIG. 1B is a block diagram illustrating the specific configuration of the region of interest output unit 106. The region of interest output unit 106 includes multiple analysis processing units (a first analysis processing unit 106a and a second analysis processing unit 106b) that perform different analysis processes in parallel on each frame of the moving image. The region of interest output unit 106 also includes a selection unit 106c that selects an appropriate region of interest based on results outputted by the multiple analysis processing units at the time at which the feature amount calculation unit 107 calculates the feature amount. The configuration of the region of interest output unit 106 is the most characteristic element of the present embodiment.

Although the first analysis processing unit 106a of the region of interest output unit 106 requires large amounts of time to perform its processing, it is capable of analyzing a single image (single frame) in detail and extracting a region of interest with high accuracy. Conversely, the second analysis processing unit 106b of the region of interest output unit 106 limits its analysis range using analysis information spanning up to the previous frame, it is thus capable of reducing the amount of time required for processing to extract a region of interest from the current frame.

The region of interest output unit 106 has the two analysis processing units, or the first analysis processing unit 106a and the second analysis processing unit 106b. The selection unit 106c scores the region of interest extraction results outputted by the two analysis processing units, and selects and holds the region of interest that most resembles a region of interest.

Figure 3:
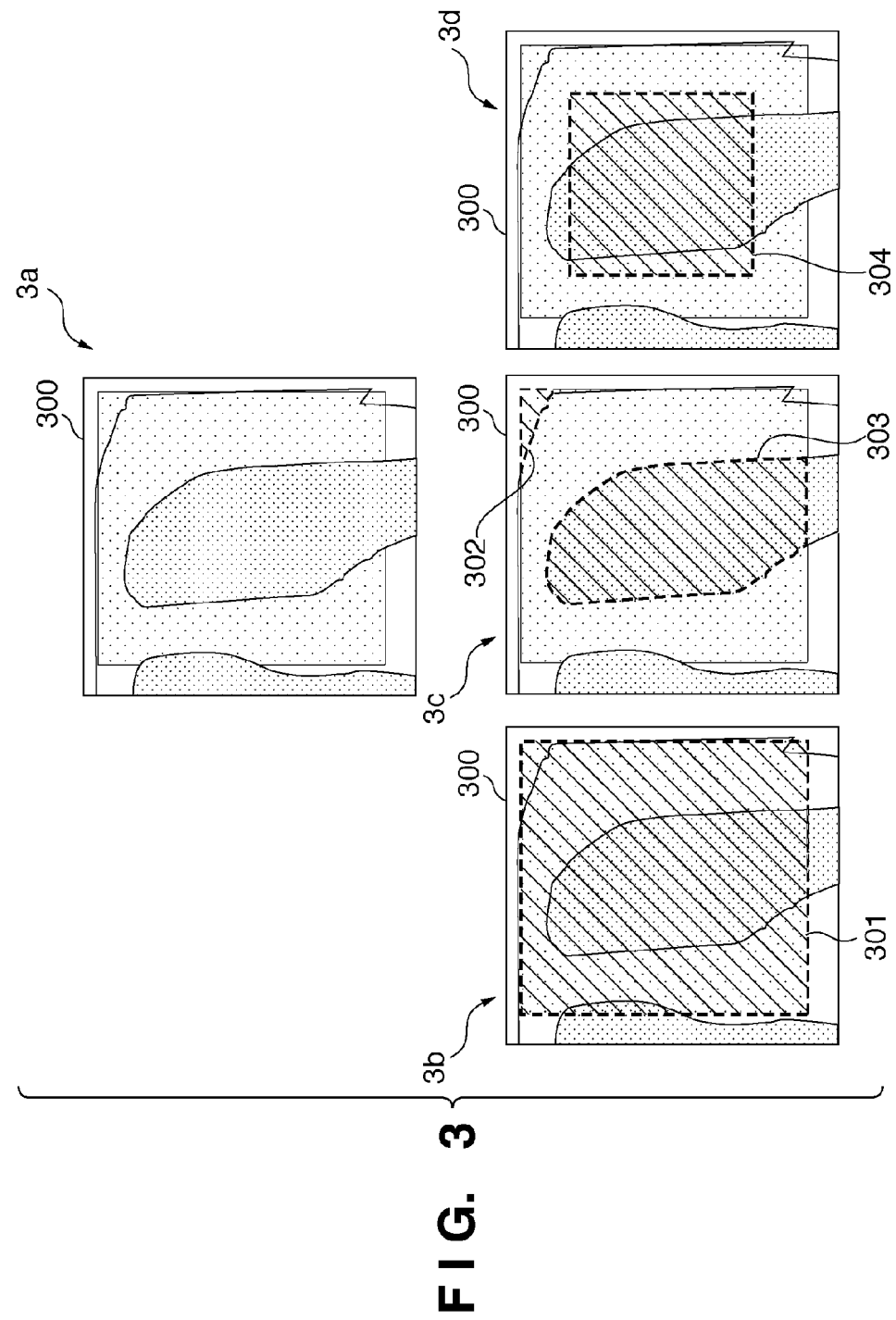
FIG. 3 is a diagram illustrating an example of extracting a region of interest.
Figure 4:
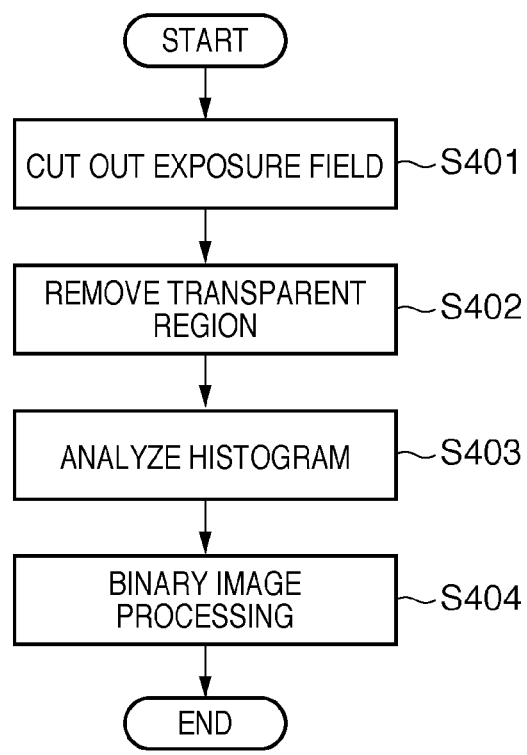
FIG. 4 is a diagram illustrating the flow of processing performed by a first analysis processing unit.

Various algorithms, depending on the region of interest as determined based on the area to be imaged and the purpose of the imaging, can be considered as algorithms suited to the first analysis processing unit 106a. In the present embodiment, the area to be imaged is assumed to be the chest area, and the descriptions herein shall take, for example, a chest area image 300 as shown in FIG. 3 (see FIG. 3-3a) as the image to be analyzed. In FIG. 3, 301 (FIG. 3-3b) indicates an exposure field region limited by a collimator (not shown) provided in the X-ray generation unit 101. 302 (FIG. 3-3c) indicates a transparent region in which X-rays have entered directly into the two-dimensional X-ray sensor 104 without passing through the object 103. 303 (FIG. 3-3c) shows the lung field region, which is the region of interest of the chest area image 300. 304 (FIG. 3-3d) indicates an example of a predetermined region inputted from the external parameter input unit 110. Here, the process for extracting the lung field region 303, which is the region of interest, from the chest area image 300 shall be described with reference to the flowchart shown in FIG. 4.

In step S401, the first analysis processing unit 106a extracts the exposure field region 301 from the chest area image 300. Generally, because there are large differences between luminance values inside and outside of the exposure field region, it is possible to detect the edges of a rectangular exposure field with ease by detecting straight line components using a Hough transform following edge detection through spatial filtering or the like. The top, bottom, left, and right ends of the exposure field edges are extracted from the chest area image 300, with the interior thereof taken as the exposure field; the exposure field region 301 is then cut out from the chest area image 300.

In step S402, the first analysis processing unit 106a removes the transparent region 302 from the cut-out exposure field region. Because the transparent region 302 is a region in which X-rays entered directly into the sensor without passing through the object, the luminance values in the transparent region are the maximum luminance values in the image, and the variance value thereof is extremely low. This region is also adjacent to the end of the exposure field in chest area imaging. Based on these properties, the transparent region is extracted and a mask created, and this region is not used in the subsequent analyses.

Figure 7:
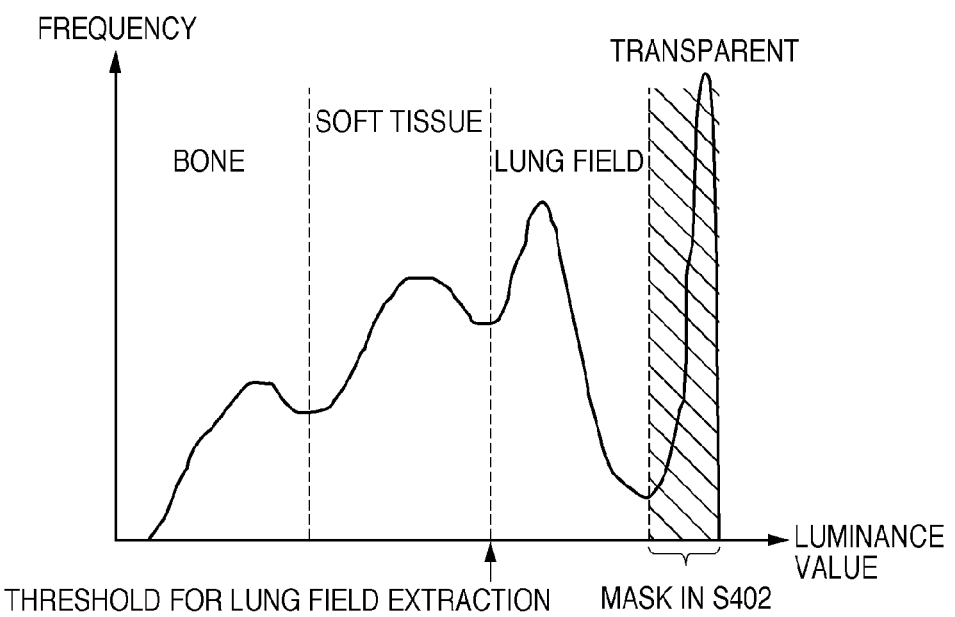

In step S403, the first analysis processing unit 106a creates a regional histogram in which the transparent region 302 is masked from the exposure field region 301. The histogram of the chest area image generally looks like that shown in FIG. 7. In this histogram, the transparent region 302 is masked through step S402 and removed from the analysis range; therefore, the lung field region 303, which is the region of interest, can for the most part be extracted through binarization using the portion of the histogram spanning from the maximum luminance value to the first valley as a threshold.

In step S404, the first analysis processing unit 106a adjusts the region extracted through the binary image processing. By performing expansion/reduction processes of morphology computation, small extraction omissions and overextracted regions can be removed, making it possible to extract the lung field region 303 as a single continuous region. The region obtained in this manner is taken as the region of interest.

Although a region of interest extraction algorithm used when taking the lung field region in the chest area image 300 as the region of interest is described here, it should be noted that the scope of the present invention is not limited thereto. For example, in radioscopy of the stomach using a barium liquid, when the stomach wall is to be extracted as the region of interest, an appropriate algorithm may be selected in accordance with the target of extraction. The processing also varies depending on the accuracy that is required. For example, if only a threshold for binarization is required, the binary image processing in step S404 is unnecessary. However, if a higher degree of accuracy is required, a method in which the area, position information, and so on of the extracted region is found and the area, position information, and so on of typical chest structures are held in a database and compared can also be considered.

An algorithm suited to the second analysis processing unit 106b limits the analysis range using the predetermined region 304 set in the external parameter input unit 110, in the case where the region of interest is extracted with the X-ray image in the first frame being the frame to be analyzed.

In the case where the region of interest is extracted with the X-ray images in the second or a subsequent frame being the frame to be analyzed, the analysis region in the frame to be analyzed is limited using the region of interest extraction results selected and held by the selection unit 106c. This algorithm ends the analysis between the X-ray irradiation and the image display.

Figure 5:
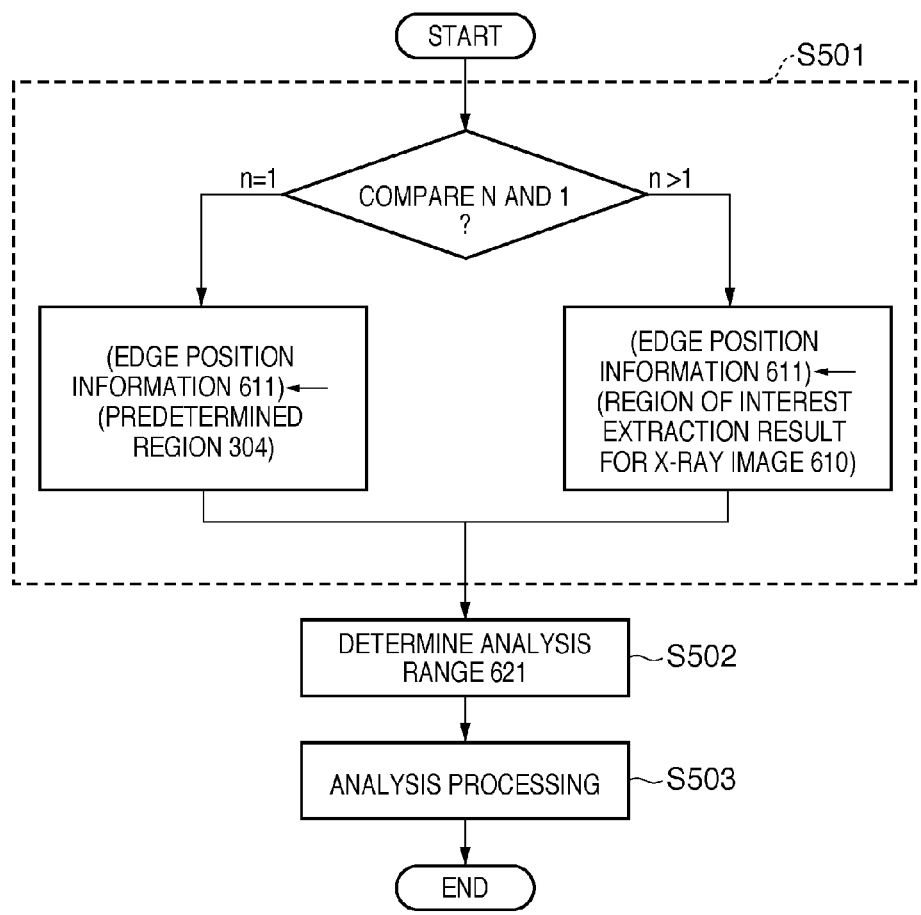
FIG. 5 is a diagram illustrating the flow of processing performed by a second analysis processing unit.

Hereinafter, an algorithm suited to the second analysis processing unit 106b shall be described with reference to FIGS. 5, 6A, and 6B.

Figure 6A:
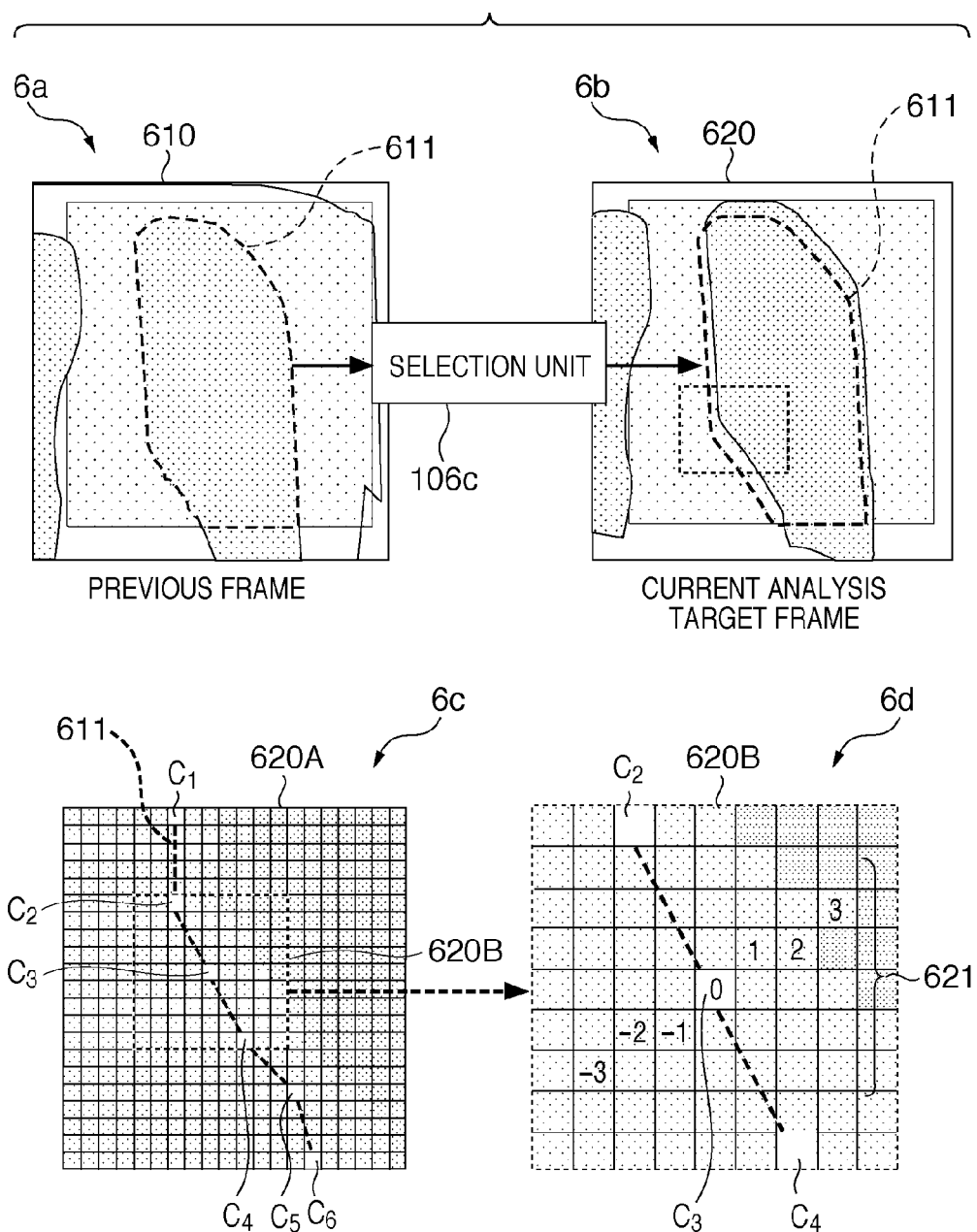
FIG. 6A is a diagram illustrating operations performed by the second analysis processing unit.
Figure 6B:
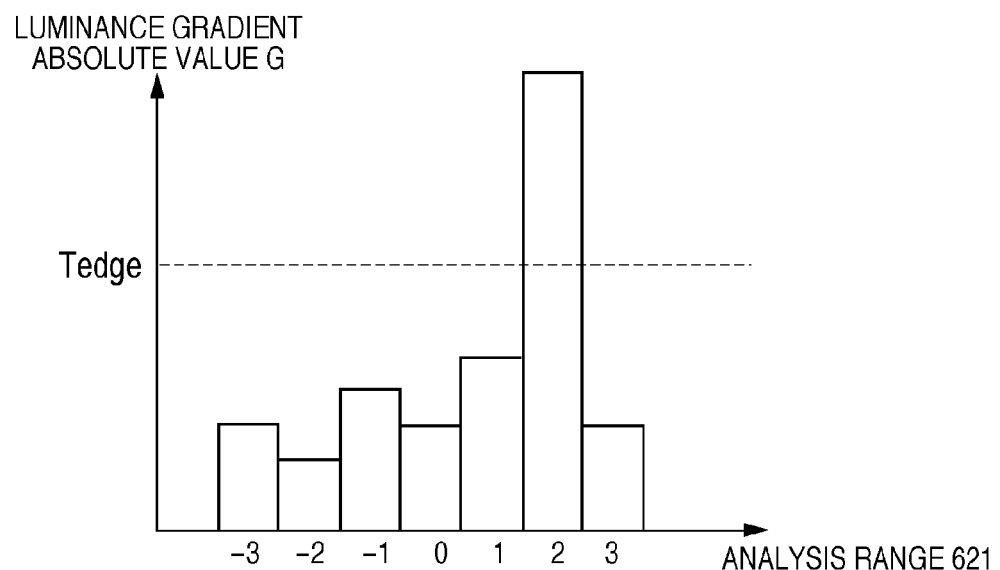
FIG. 6B is a diagram illustrating operations performed by the second analysis processing unit.

In step S501, the second analysis processing unit 106b extracts a region of interest from the X-ray image in the nth frame (where n=1, 2, 3, 4, and so on) as an analysis target frame 620 (see FIG. 6A-6b).

In order to extract the region of interest, when n=1, the region of interest extraction result for the predetermined region 304 is projected upon the analysis target frame 620 as edge position information 611. Meanwhile, when n>1, the region of interest extraction result for an n−1th frame 610, which is the frame previous to the nth frame (see FIG. 6A-6a) and is held in the selection unit 106c, is projected upon the analysis target frame 620 as the edge position information 611.

Here, the edge position information 611 is expressed by N number of control points $C_i=(X_i, Y_i)$, obtained by sampling the edge pixels of the region of interest every five pixels. "Projection" refers to reading out the coordinates of these N control points $C_i=(X_i, Y_i)$ onto the analysis target frame in order to determine the next analysis range. Note that when the region of interest is the closed curved line, the control points $C_N$ and $C_i$ are adjacent to each other.

In step S502, the second analysis processing unit 106b finds the analysis ranges for each control point $C_i$ in the edge position information 611 projected upon the analysis target frame 620 (see FIG. 6A-6b). FIG. 6A-6c is an enlarged view of a partial region 620A of FIG. 6A-6b, and FIG. 6A-6d is an enlarged view of a partial region 620B of FIG. 6A-6c. Here, the analysis range for $C_i=(X_i, Y_i)$ is seven pixels on a straight line, passing through a pixel $(x_i, y_i)$ corresponding to control point $C_3$, that connects $C_{i-1}=(x_{i-1}, Y_{i-1})$ and $C_{i+1}=(x_{i+1}, y_{i+1})$, with the pixel $(x_i, y_i)$ at the center. (FIG. 6A-6d)

In step S503, the second analysis processing unit 106b calculates a luminance gradient absolute value $G(x, y)$ for a pixel $(x, y)$ in an analysis range 621 for each control point $C_i$. Here, this calculation is performed through Formula (1), using an experimentally-obtained threshold $T_{edge}$.

$$G(x,y) > T_{edge} \qquad (1)$$

The second analysis processing unit 106b finds the pixel (x, y) that fulfills the relationship in Formula (1), and when there are more than one, takes the pixel with the maximum value as an edge point in the analysis target frame 620, and updates the control point $C_i$ with those coordinates. FIG. 6B is a diagram illustrating the results of comparing the luminance gradient absolute value $G(x, y)$ and $T_{edge}$ for each of the seven pixels in FIG. 6A-6d. The luminance gradient absolute value G of the +2th pixel exceeds the threshold $T_{edge}$.

There are situations where there are no pixels in the analysis range 621 for the control point $C_i$ that satisfy Formula (1), such as in the case where the object has experienced a large movement between the n−1th frame 610 and the analysis target frame 620 and the case where the edge position information 611 of the first frame is the predetermined region 304 provided by the external parameter input unit.

The control point $C_i$ is not updated with the new pixel coordinates at this time. The edge points in the analysis target frame 620 are found for all of the N control points $C_i$, and with respect to the control points that are to be updated, the result of performing linear interpolation on the N control points $C_i$ that have been updated is taken as an extraction result 622 for the analysis target frame 620.

Although the edges of the analysis target frame are extracted using only the luminance gradient absolute values in the edges in the analysis range, the area of the region of interest that defines the edge form and edge components, setting values for external parameters that take into account possible distortion in the region of interest, and so on may also be used. Furthermore, although the above descriptions discuss linear interpolation between each control point in light of the processing time, if there is leeway in terms of processing time and more favorable extraction results are required, the interpolation may be performed using a curve, as with spline interpolation and the like.

The first analysis processing unit 106a can perform detailed analysis on a single image, and is capable of extracting a region of interest with high accuracy. However, the first analysis processing unit 106a generally takes a long time to output a region of interest extraction result. For example, in a 30 fps X-ray radioscopy device, there are cases where the analysis is not finished by the time the image is displayed following X-ray irradiation. It is therefore desirable to use the results of the second analysis processing unit 106b, which outputs the analysis results in real time, until the analysis performed by the first analysis processing unit 106a is completed.

The second analysis processing unit 106b extracts the region of interest at high speeds, and thus can extract the region of interest in accordance with minute movements of the object. However, because the analysis is performed on a limited range and with a simple algorithm, there are regions of interest that cannot be extracted using an algorithm suited to the second analysis processing unit 106b, and thus there is the possibility of mistaken extractions. Therefore, when highly-accurate extraction results are required even if obtaining such results takes a long time, the results of the first analysis processing unit 106a are favorable.

The selection unit 106c constantly holds a single region of interest extraction result. When a new region of interest extraction result is outputted from the multiple analysis processing units, the selection unit 106c calculates an evaluation value that scores how evident a region of interest is in the processing target frame at that point in time in the region of interest extraction result that is being held and the new region of interest extraction result.

Here, an evaluation value S is defined by Formula (2), where the coordinates of a pixel contained in the edge of the region of interest extraction result is $(x, y) \in E$, the number of pixels contained in the edge is Num, and the luminance gradation absolute value for the coordinates (x, y) in the processing target frame is $G(x, y)$.

(Equation 1)

$$S = \frac{\sum_{(x,y)\in E} G(x, y)}{Num} \qquad (2)$$

Figure 8:
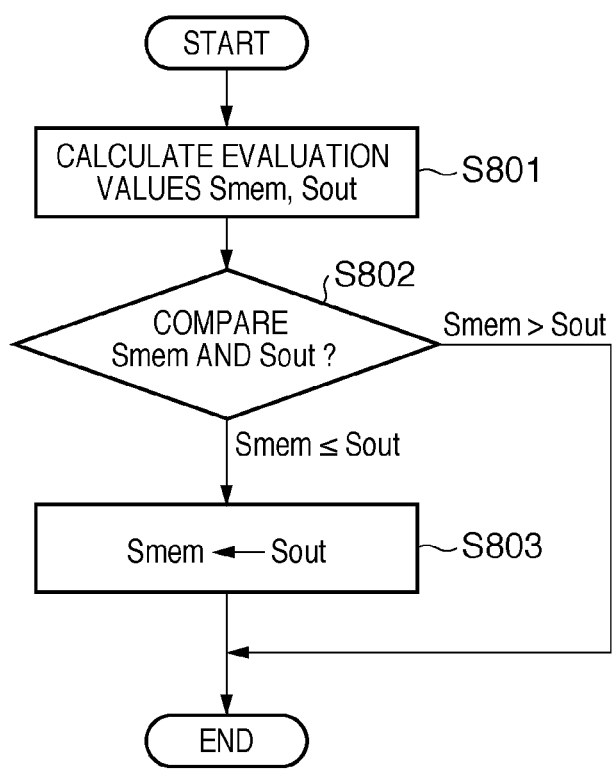
FIG. 8 is a diagram illustrating the flow of processing performed by a selection unit.

Formula (2) expresses the average edge strength of the region of interest extraction result in the processing target frame. A process by which the selection unit 106c selects a region of interest extraction result using this evaluation value S shall be described with reference to FIG. 8.

In step S801, the selection unit 106c calculates the stated evaluation value $S_{out}$ from the pixel $(x, y) \in E_{out}$ contained in the edge of an outputted region of interest extraction result at the timing at which the first analysis processing unit 106a or the second analysis processing unit 106b outputs a region of interest extraction result. Furthermore, the selection unit 106c calculates an evaluation value $S_{mem}$ for the processing target frame at that point in time from the pixel (x, y) ∈$E_{mem}$ contained in the edge of the region of interest extraction result held by the selection unit 106c.

In step S802, the evaluation values $S_{out}$ and $S_{mem}$ calculated in step S801 are compared.

In step S803, if the result of the comparison performed in step S802 fulfills the relationship shown in Formula (3), the selection unit 106c replaces the held region of interest extraction result with the newly-outputted region of interest extraction result.

$$S_{out} \geq S_{mem} \quad (3)$$

Because the edge of the region of interest can generally be thought of as having a high strength, selecting the result that has the higher strength using the average edge strength as the evaluation value makes it possible to select the region of interest extraction result that most resembles a region of interest in the analysis target frame. The region of interest extraction result held by the selection unit 106c is read out during the operations of the second analysis processing unit 106b and during the operations of the feature amount calculation unit 107, and is used in the respective processes performed thereby.

Note that the selection unit 106c defines an evaluation value that scores how evident a region of interest is as the average edge strength in the region of interest extraction result. However, it is also possible to use at least one of the following for evaluation computation: the edge strength, edge length, edge luminance, and edge position of the region of interest extraction result; the luminance, form, central position, area, and average luminance value of the region of interest; and a variance value of the region of interest.

The operations performed by the units according to the present embodiment as described thus far shall be described with reference to FIGS. 2 and 9, using up to the fourth frame as an example. Note that it is assumed that a two-frame delay arises in the first analysis processing unit 106a by the time the analysis results are outputted.

Figure 2:
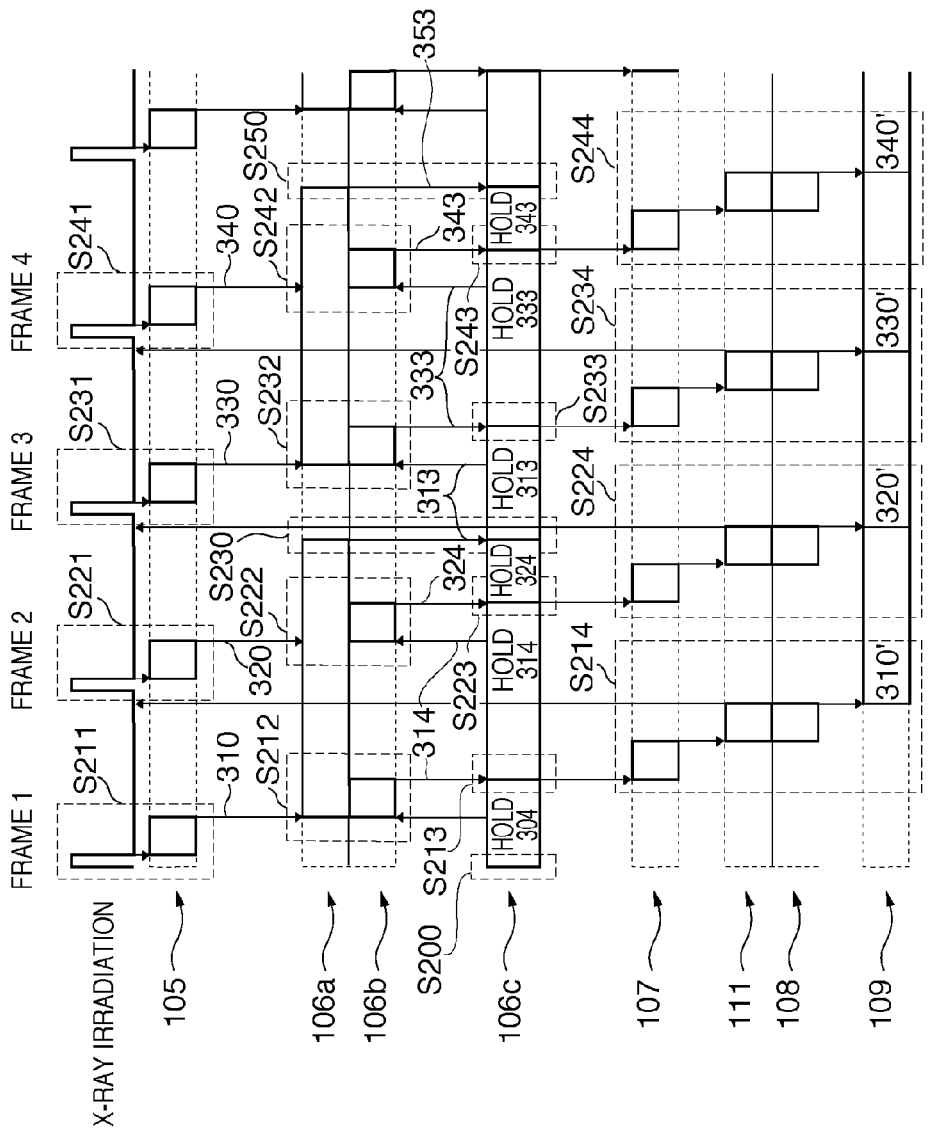
FIG. 2 is a timing chart illustrating a flow of processing according to the first embodiment.
Figure 9:
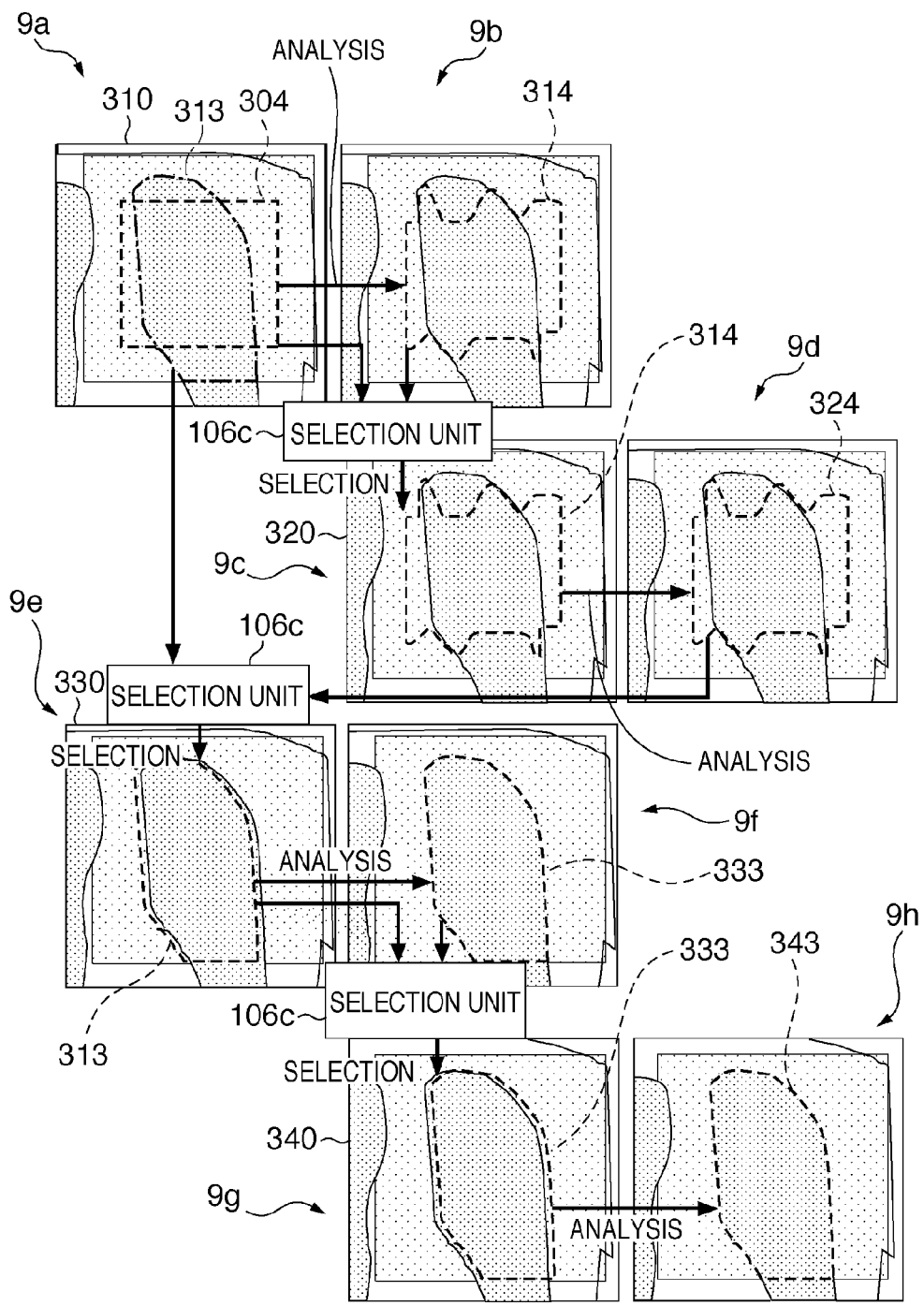
FIG. 9 is a diagram illustrating a region of interest extraction process according to the first embodiment.

In step S200 of FIG. 2, prior to the start of the X-ray radioscopy, the predetermined region 304 is set in the external parameter input unit 110 (FIG. 9-9a). The predetermined region 304 may be inputted directly as the form of region of interest through operations such as mouse operations performed by a physician, or may be specified as a region that has a certain form and size in the central portion of the image. In moving picture imaging where the object moves, as in X-ray radioscopy, it is not possible to update the region of interest appropriately based on the movement in each frame through input made from the exterior. Normally, a setting such as a rectangular region that takes up, for example, 50% of the total image in the central portion is made when the radioscopy is commenced, and is not updated in real time during radioscopy. Generally, X-ray imaging is carried out so that portions important for diagnostic purposes are located in the center of the image, and thus while the predetermined region is not extensively different from the region of interest, it is not optimal. Here, as shown in FIG. 9-9a, it is assumed that the predetermined region 304 is held by the selection unit 106c as the rectangular region in the central portion of the image.

In step S211, the X-ray radioscopy imaging commences, and the X-ray generation unit 101 irradiates the object 103 with the first pulse of X-rays 102 (see FIG. 1A). The X-rays 102 permeate the object 103 while being attenuated, and enter into the two-dimensional X-ray sensor 104; the two-dimensional X-ray sensor 104 outputs the first frame of an X-ray image. The pre-processing unit 105 performs pre-processing, such as offset correction processing, gain correction processing, and so on on the X-ray image outputted from the two-dimensional X-ray sensor 104. This is taken as an X-ray image 310 (FIG. 9-9a).

In step S212, the region of interest output unit 106 commences the process for extracting a region of interest from the X-ray image 310 on which the pre-processing unit 105 performed pre-processing. The first analysis processing unit 106a then commences its analysis process, but the region of interest extraction result is outputted two frames later.

Then, because the current frame is the first frame, the second analysis processing unit 106b performs its analysis processing using the edge position information of the predetermined region 304, in accordance with the algorithm described using FIGS. 6A and 6B, and outputs a region of interest extraction result 314 (FIG. 9-9b). At this time, because the edge position information used by the second analysis processing unit 106b is the predetermined region 304 set by the external parameter input unit, it cannot be guaranteed that an edge that should be extracted is present in the analysis range defined by the control points, and in many cases, the control point coordinates are not updated. As a result, out of the edges of the predetermined region 304 indicated by 314 in FIG. 9-9b, only the edges in the vicinity of the lung field edges are corrected; as for the edges that are at a distance from the lung field edges, which have not moved from the edges of the predetermined region 304, are outputted as the region of interest extraction result 314 (FIG. 9-9b).

In step S213, the selection unit 106c calculates the evaluation values $S_{mem}$ and $S_{out}$ in the X-ray image 310 for the region of interest extraction result 314 held in the selection unit 106c and the region of interest extraction result 314 outputted from the second analysis processing unit 106b, respectively. If this is performed in accordance with the algorithm suited to the second analysis processing unit 106b, the result can generally be thought of as $S_{mem} \leq S_{out}$. Therefore, the predetermined region 304 held by the selection unit 106c is replaced with the region of interest extraction result 314. The region of interest extraction result 314 is then held in the selection unit 106c.

In step S214, the feature amount calculation unit 107 reads out the region of interest extraction result 314 held in the selection unit 106c at the time when operations commence, and calculates the feature amount. Using this feature amount, the image processing unit 108 performs image processing on the X-ray image 310 and outputs the resultant as a processed image 310' through the image display unit 109, after which the X-ray control unit 111 calculates the X-ray conditions for the second pulse; the processing of the first frame thus ends.

In step S221, the X-ray generation unit 101 irradiates the object 103 with the second pulse of X-rays 102; the same processing as in step S211 is performed up to the pre-processing, and an X-ray image 320 is outputted (FIG. 9-9c).

In step S222, the region of interest output unit 106 commences the process for extracting a region of interest from the X-ray image 320. Because the analysis processing performed by the first analysis processing unit 106a on the X-ray image 310 has not yet ended, that process is continued. Then, the second analysis processing unit 106b performs its analysis processing using the edge position information of the region of interest extraction result 314 held in the selection unit 106c, in accordance with the algorithm described using FIGS. 6A and 6B, and outputs a region of interest extraction result 324 (FIG. 9-9d).

In step S223, the selection unit 106c calculates the evaluation values $S_{mem}$ and $S_{out}$ in the X-ray image 320 for the region of interest extraction result 314 held in the selection unit 106c and the region of interest extraction result 324 outputted from the second analysis processing unit 106b, respectively. Here, assuming that $S_{mem} \leq S_{out}$, the region of interest extraction result 314 held by the selection unit 106c is replaced with the region of interest extraction result 324. The region of interest extraction result 324 is then held in the selection unit 106c.

In step S224, the feature amount calculation unit 107 reads out the region of interest extraction result 324 held in the selection unit 106c at the time when operations commence, and calculates the feature amount. Using this feature amount, the image processing unit 108 performs image processing on the X-ray image 320 and outputs the resultant as a processed image 320' through the image display unit 109, after which the X-ray control unit 111 calculates the X-ray conditions for the third pulse; the processing of the second frame thus ends.

In step S230, the first analysis processing unit 106a ends its processing, and outputs a region of interest extraction result 313. The selection unit 106c calculates the evaluation values $S_{mem}$ and $S_{out}$ in the X-ray image 320 for the region of interest extraction result 324 held in the selection unit 106c and the region of interest extraction result 313 outputted from the first analysis processing unit 106a, respectively. This region of interest extraction result is the result of performing detailed analysis on all pixels in 313. In general, it can be thought that the region of interest extraction result 313 obtains more desirable results than the region of interest extraction results 314 and 324, which are the results of analysis processes limited to the vicinity of the edge position information in the predetermined region 304. In this case, $S_{mem} \leq S_{out}$. Therefore, the region of interest extraction result 324 held by the selection unit 106c is replaced by the region of interest extraction result 313 outputted by the first analysis processing unit 106a. The region of interest extraction result 313 is then held in the selection unit 106c.

In step S231, the X-ray generation unit 101 irradiates the object 103 with X-rays 102 using the X-ray conditions of the third pulse, thereby generating the image of the third frame. The pre-processing unit 105 performs pre-processing on this generated image, resulting in an X-ray image 330 (FIG. 9-9e).

In step S232, in the region of interest output unit 106, the first analysis processing unit 106a, which has finished its analysis processing on the X-ray image 310, commences analysis processing on the X-ray image 330. The second analysis processing unit 106b outputs a region of interest extraction result 333 from the X-ray image 330 by performing analysis processing using the region of interest extraction result 313 held in the selection unit 106c.

In step S233, the selection unit 106c calculates the evaluation values $S_{mem}$ and $S_{out}$ in the X-ray image 330 for the region of interest extraction result 313 held in the selection unit 106c and the region of interest extraction result 333 outputted from the second analysis processing unit 106b, respectively. Considering that the region of interest extraction result 313 is the result of analyzing the X-ray image 310 in the first frame, and the region of interest extraction result 333 is the result of analyzing the X-ray image 330 in the third frame, or the current processing target, generally, $S_{mem} \leq S_{out}$. Therefore, the region of interest extraction result 313 held by the selection unit 106c is updated to the region of interest extraction result 333 outputted by the second analysis processing unit 106b (FIG. 9-9f). The region of interest extraction result 333 is then held in the selection unit 106c.

In step S234, the feature amount calculation unit 107 reads out the region of interest extraction result 333 held in the selection unit 106c at the time when operations commence, and calculates the feature amount. Using this feature amount, the image processing unit 108 performs image processing on the X-ray image 330 and outputs the resultant as a processed image 330' through the image display unit 109. The X-ray control unit 111 then calculates the X-ray conditions for the fourth pulse, and the processing of the third frame thus ends.

In step S241, the X-ray generation unit 101 irradiates the object 103 with the fourth pulse of X-rays 102; the pre-processing unit 105 performs pre-processing on the generated image, and an X-ray image 340 is outputted.

In step S242, the region of interest output unit 106 commences the process for extracting a region of interest from the X-ray image 340. Because the analysis processing performed by the first analysis processing unit 106a on the X-ray image 330 has not yet ended, that process is continued. Then, the second analysis processing unit 106b performs its analysis processing using the edge position information of the region of interest extraction result 333 held in the selection unit 106c, in accordance with the algorithm described using FIGS. 6A and 6B, and outputs a region of interest extraction result 343 (FIG. 9-9g).

In step S243, the selection unit 106c calculates the evaluation values $S_{mem}$ and $S_{out}$ in the X-ray image 340 for the region of interest extraction result 333 held in the selection unit 106c and the region of interest extraction result 343 outputted from the second analysis processing unit 106b, respectively. Here, assuming that $S_{mem} \leq S_{out}$, the region of interest extraction result 333 held by the selection unit 106c is replaced with the region of interest extraction result 343 (FIG. 9-9h). The region of interest extraction result 343 is then held in the selection unit 106c.

In step S244, the feature amount calculation unit 107 reads out the region of interest extraction result 343 held in the selection unit 106c at the time when operations commence, and calculates the feature amount. Using this feature amount, the image processing unit 108 performs image processing on the X-ray image 340 and outputs the resultant as a processed image 340' through the image display unit 109, after which the X-ray control unit 111 calculates the X-ray conditions for the fifth pulse; the processing of the fourth frame thus ends.

In step S250, the first analysis processing unit 106a ends its processing, and outputs a region of interest extraction result 353. The selection unit 106c calculates the evaluation values $S_{mem}$ and $S_{out}$ in the X-ray image 340 for the region of interest extraction result 343 held in the selection unit 106c and the region of interest extraction result 353 outputted from the first analysis processing unit 106a, respectively. Here, the region of interest extraction result 333 is the result of analysis performed on the X-ray image 330, and thus delay occurs. However, the region of interest extraction result 343 is the result of analysis performed on the X-ray image 340, and thus delay does not occur. Therefore, if the processing of the second analysis processing unit 106b has ended normally and a favorable extraction result has been obtained, then $S_{mem} > S_{out}$, and thus the region of interest extraction result held in the selection unit 106c is not updated here. However, in the case where there is almost no movement in the object between the X-ray image 330 and the X-ray image 340, or the case where the second analysis processing unit 106b has performed a mistaken extraction, then $S_{mem} \leq S_{out}$, and thus the region of interest extraction result 343 held in the selection unit 106c is replaced with the region of interest extraction result 353.

According to the present embodiment, it is possible to extract, in real time, a region of interest for calculating a feature amount used in image processing, X-ray control, and so on in the capturing of a moving picture as exemplified by X-ray radioscopy.

The two analysis processes performed by the first analysis processing unit 106a and the second analysis processing unit 106b, whose processing times differ, are performed in parallel. The selection unit 106c then evaluates the outputted analysis results and the region of interest extraction result held in the selection unit 106c at the time at which the respective analysis results are outputted, selects the more appropriate result, and holds that result. Through this, it is possible to select the more appropriate region of interest when executing processing in which a region of interest extraction result is required in each frame of a high-frame rate moving picture.

Here, the elements shown in FIGS. 1A and 1B may be configured of dedicated hardware, but it is also possible to realize the functional configuration of this hardware through software. In such a case, the functions of the elements shown in FIGS. 1A and 1B can be realized by installing software in an information processing apparatus and using the computational functionality of the information processing apparatus to implement a moving picture processing method by executing the software. By executing this software, for example, an analysis processing step, in which the different analysis processes are performed in parallel on each frame that makes up a moving image and a region of interest defined as a portion of an object subjected to radioscopy by X-ray irradiation is extracted from each frame, is performed. Then, a selection step, in which evaluation operations are performed on the multiple regions of interest extracted based on the different analysis results, a single region of interest is selected from the multiple regions of interest extracted in the analysis processing step based on the result of the evaluation operations, and the region of interest is outputted, is performed.

Figure 12:
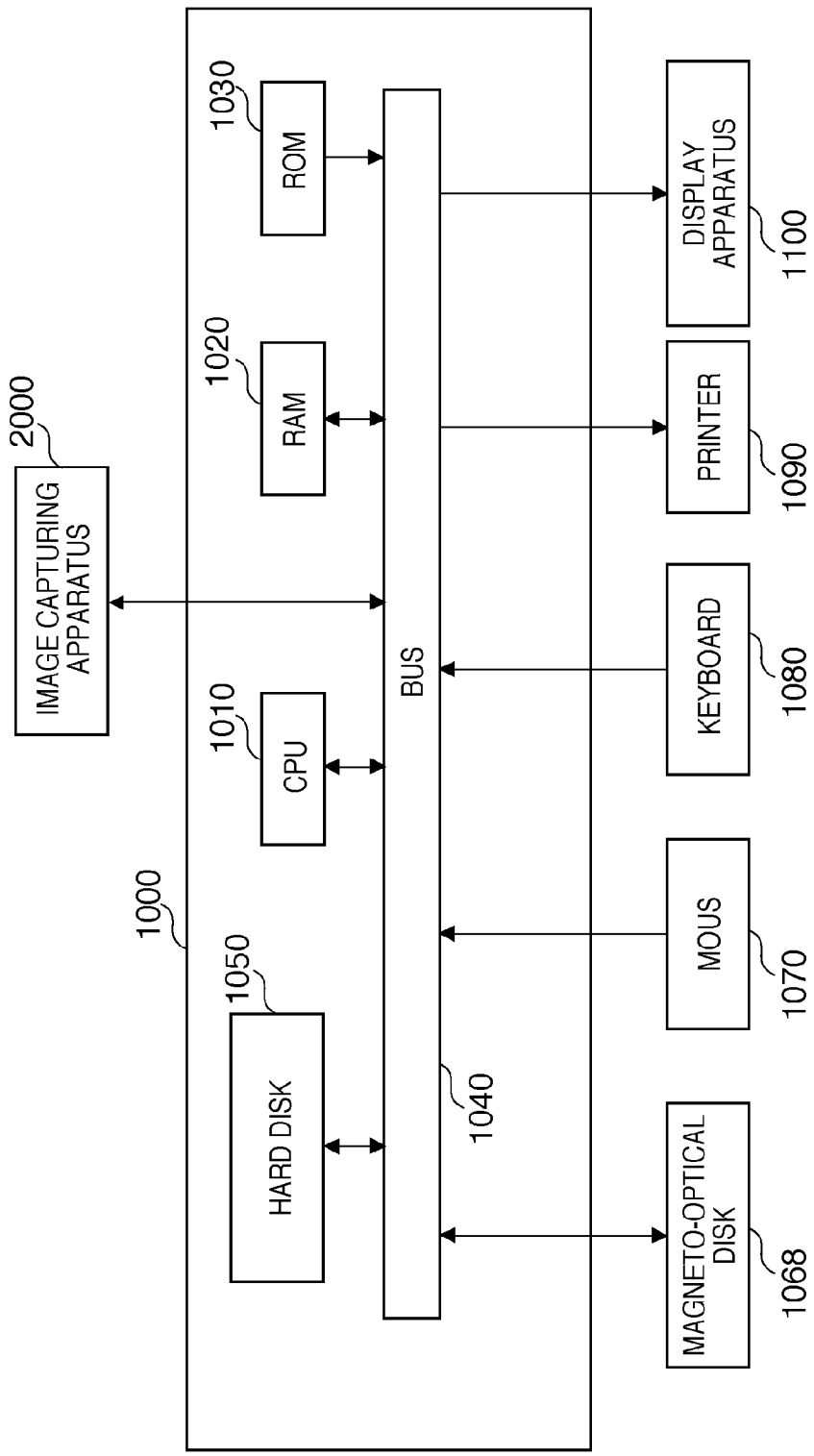
FIG. 12 is a diagram illustrating an example of a computer system capable of realizing the present invention.

FIG. 12 is a block diagram illustrating the hardware configuration of an information processing apparatus and the configuration of peripheral devices thereof. An information processing apparatus 1000 is connected to an image capturing apparatus 2000, and the configuration is such that the two devices can perform data communication with each other.

(Information Processing Apparatus)

A CPU 1010 performs overall control of the information processing apparatus 1000 using programs and data stored in a RAM 1020 and a ROM 1030, and is capable of executing operational processes regarding predetermined image processing through the execution of such programs.

The RAM 1020 includes an area for temporarily storing programs and data loaded from a magneto-optical disk 1068, a hard disk 1050, or the like. Furthermore, the RAM 1020 includes an area for temporarily storing image data and the like obtained from the image capturing apparatus 2000. The RAM 1020 also includes a working area used by the CPU 1010 when executing various processes. The ROM 1030 stores setting data, a boot program, and so on for the information processing apparatus 1000.

The hard disk 1050 holds an OS (operating system) as well as programs and data for causing the CPU 1010 to execute the processes performed by the elements illustrated in FIGS. 1A and 1B. These are loaded into the RAM 1020 as appropriate under the control of the CPU 1010, and are then processed by the CPU 1010. It is also possible to store moving image data in the hard disk 1050.

The magneto-optical disk 1068 is an example of an information storage medium, and it is possible to store part or all of the programs and data saved in the hard disk 1050 in this magneto-optical disk 1068.

A mouse 1070 and keyboard 1080 can input various instructions to the CPU 1010 through operations performed by the operator of the information processing apparatus 1000. For example, inputting the predetermined region 304 to the external parameter input unit 110 shown in FIG. 1A can be performed by using the mouse 1070 or the keyboard 1080.

A printer 1090 is capable of printing images displayed upon the image display unit 109 onto a recording medium and outputting the resultant.

A display apparatus 1100 is configured of a CRT display, a liquid-crystal display, or the like, and is capable of displaying the results of processing performed by the CPU 1010 as images, text, and so on. For example, the display apparatus 1100 can display images processed by the elements shown in FIGS. 1A and 1B and ultimately outputted from the image display unit 109. In this case, the image display unit 109 functions as a display control unit for displaying images on the display apparatus 1100. A bus 1040 connects the elements within the information processing apparatus 1000, and is capable of sending and receiving data among those elements.

(Image Capturing Apparatus 2000)

Next, the image capturing apparatus 2000 shall be described. The image capturing apparatus 2000 is a device capable of capturing moving images, such as an X-ray radioscopy device; the captured image data is sent to the information processing apparatus 1000. Note that plural pieces of the image data can be sent altogether to the information processing apparatus 1000, or can be sent sequentially, as it is captured. In addition, settings for the X-ray irradiation conditions of the next frame, image capturing commands, and so on to be performed by the X-ray control unit 111 shown in FIG. 1A are sent from the information processing apparatus 1000. The image capturing apparatus 2000 can update the set image capturing conditions based on the received X-ray irradiation conditions of the next frame, image capturing commands, and so on, and capture the image data.

Second Embodiment

Figure 10:
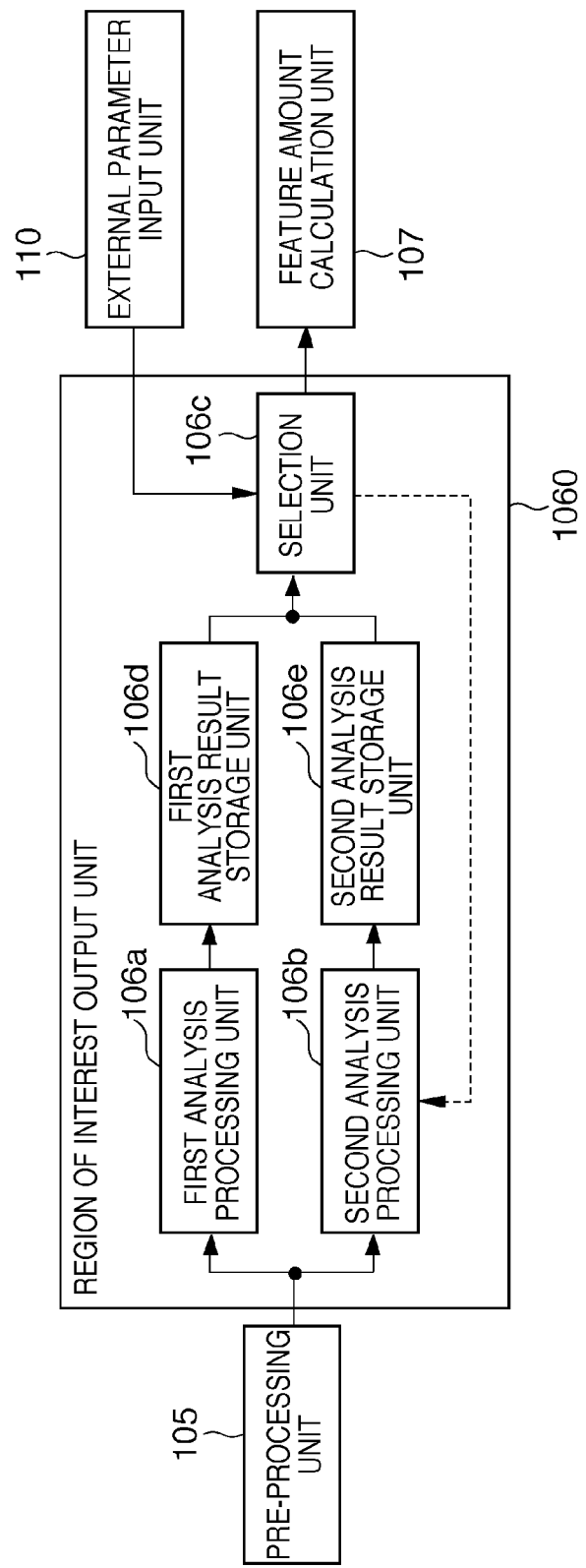
FIG. 10 is a diagram illustrating the configuration of an X-ray radioscopy device according to a second embodiment.

A second embodiment of the present invention shall be described next with reference to FIG. 10. In FIG. 10, the pre-processing unit 105 and the external parameter input unit 110 are the same as those described in the first embodiment, and thus descriptions thereof shall be omitted to avoid prolixity.

A region of interest output unit 1060 according to the present embodiment includes a first analysis processing unit 106a that, although requiring a long time to perform its processing, analyzes a single image in detail and extracts a region of interest with high accuracy. The region of interest output unit 1060 also includes a second analysis processing unit 106b that reduces the amount of time required for processing to extract a region of interest from the current frame by limiting its analysis range using analysis information spanning up to the previous frame. The region of interest output unit 1060 also includes a first analysis result storage unit 106d that holds the result of the analysis performed by the first analysis processing unit 106a and a second analysis result storage unit 106e that holds the result of the analysis performed by the second analysis processing unit 106b. The region of interest output unit 1060 also has a selection unit 106c that reads out data from the first analysis result storage unit 106d and the second analysis result storage unit 106e at the time when the region of interest extraction result are necessary, selects the result that most resembles a region of interest by comparing the data, and outputs the selected result.

Each time the first analysis processing unit 106a outputs an analysis result, the first analysis result storage unit 106d replaces the analysis result currently held with the new analysis result, and holds the new analysis result. Meanwhile, each time the second analysis processing unit 106b outputs an analysis result, the second analysis result storage unit 106e replaces the analysis result currently held with the new analysis result, and holds the new analysis result. The selection unit 106c reads out the data held in the first analysis result storage unit 106d and the second analysis result storage unit 106e at the time when the second analysis processing unit 106b or a feature amount calculation unit 107 requires a region of interest extraction result. Based on the read-out data, the selection unit 106c then calculates evaluation values S1 and S2, which score how closely the data resembles a region of interest. The selection unit 106c then compares the calculation results, selects the result with the higher evaluation value as the region of interest, and outputs the region of interest to the second analysis processing unit 106b or the feature amount calculation unit 107.

According to the present embodiment, it is possible to extract, in real time, a region of interest for calculating a feature amount used in image processing, X-ray control, and so on in the capturing of a moving picture as exemplified by X-ray radioscopy.

The two analysis processes performed by the first analysis processing unit 106a and the second analysis processing unit 106b, whose processing times differ, are performed in parallel, and the analysis results are held in the first analysis result storage unit 106d and the second analysis result storage unit 106e, respectively. These analysis results are read out by the selection unit 106c at the time when they are necessary, and the more appropriate result, as determined by comparing the evaluation values thereof, is selected as the region of interest and outputted. Through this, it is possible to use the more appropriate region of interest when executing processing in which a region of interest extraction result is required in each frame of a high-frame rate moving picture.

Third Embodiment

Figure 11:
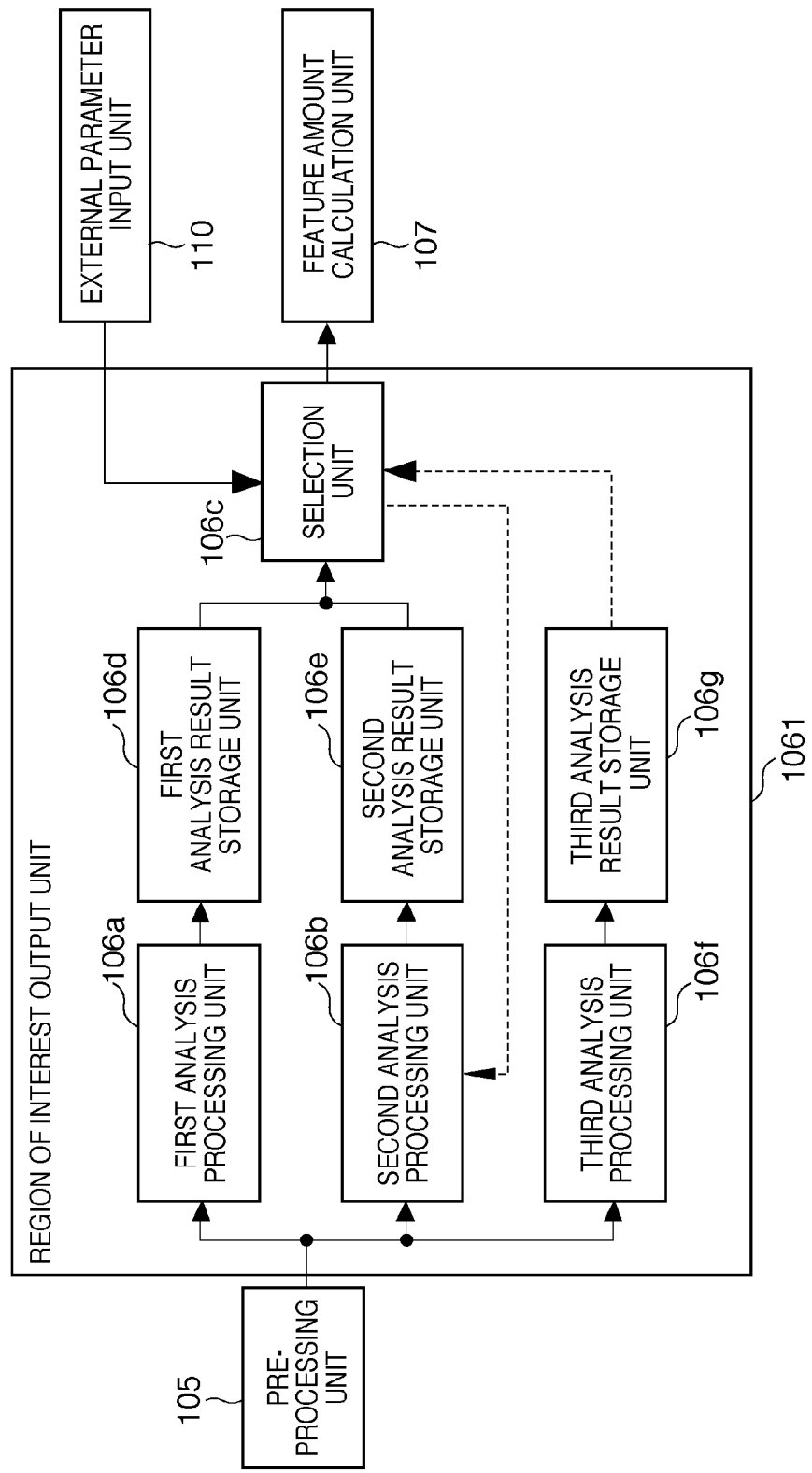
FIG. 11 is a diagram illustrating the configuration of an X-ray radioscopy device according to a third embodiment.

A third embodiment of the present invention shall be described next with reference to FIG. 11. In FIG. 11, the pre-processing unit 105 and the external parameter input unit 110 are the same as those described in the first embodiment, and thus descriptions thereof shall be omitted to avoid prolixity.

A region of interest output unit 1061 according to the present embodiment has a configuration equivalent to adding a third analysis processing unit 106f that detects movement of an object and a third analysis result storage unit 106g that holds that analysis result to the region of interest output unit 1060 of the second embodiment. The result of detecting the movement is applied when a selection unit 106c selects a region of interest.

Assuming the current analysis target is the image in the nth frame, the movement Mn of the object relative to the previous n−1th frame can be expressed using Formula (4). Here, the motion detection range in the image in the nth frame (for example, 50×50 pixels in the center of the image) is taken as An, and the luminance value at coordinates (x, y) in the image in the nth frame is expressed as In(x, y).

(Equation 2)

$$M_n = \sum_{(x,y) \in A_n} |I_n(x, y) - I_{n-1}(x, y)| \quad (4)$$

Formula (4) expresses how much the luminance value in the motion detection range has changed between frames, and thus Mn indicates the degree of motion of the object. Here, using experimentally-obtained thresholds T1 and T2 (where T1<T2), when the relationship indicated in Formula (5) holds true, it is assumed that there is almost no object motion between the frames.

$$Mn < T1 \quad (5)$$

At this time, it can be thought that delay in the outputted result arising at the first analysis processing unit 106a has no influence, and thus the selection unit 106c can use the result from the first analysis processing unit 106a.

$$T1 \leq Mn < T2 \quad (6)$$

When the relationship indicated in Formula (6) holds true, it is assumed that a minute amount of object motion has occurred between the frames, capable of being extracted by the second analysis processing unit 106b. At this time, the result from the second analysis processing unit 106b is more appropriate than the result from the first analysis processing unit 106a.

$$T2 \leq Mn \quad (7)$$

When the relationship indicated in Formula (7) holds true, it is assumed that a large amount of object motion has occurred at the nth frame, rendering even the second analysis processing unit 106b incapable of extracting a region of interest. Furthermore, when the first analysis processing unit 106a is executing its analysis processing on an image in a frame previous to the n−1th frame, those results are meaningless beyond the nth frame in which a large object motion has occurred, occasionally resulting in a major error. Therefore, it is preferable to update the region of interest extraction result held in the selection unit 106c with the predetermined region 304 inputted through the external parameter input unit 110.

By using the analysis results of the first analysis processing unit 106a and the second analysis processing unit 106b together to make a determination based on the abovementioned motion detection results, the selection unit 106c can improve the accuracy of the region of interest extraction result selection.

Furthermore, when a large amount of motion has been detected in the object, the region of interest held in the selection unit 106c is overwritten by the predetermined region 304 set through the external parameter input unit 110. This makes it possible to suppress the extraction of region of interest in which it is possible that a large extraction error has occurred, erroneous operations in image processing and X-ray control that can occur due to inappropriate feature amount calculations, and so on.

Other Embodiments

Note that it goes without saying that the object of the present invention can also be achieved by supplying, to a system or apparatus, a computer-readable storage medium in which a software program that realizes the functions of the aforementioned embodiments has been stored. It also goes without saying that the object of the present invention can also be achieved by loading and executing the program stored in the storage medium using a computer (or CPU or MPU) of the system or apparatus.

In this case, the program itself that is loaded from the storage medium realizes the functions of the above-described embodiment, and the storage medium that stores the program achieves the present invention.

Examples of the storage medium that can be used to supply the program include flexible disks, hard disks, optical disks, magneto-optical disks, CD-ROMs, CD-Rs, non-volatile memory cards, ROMs, and so on.

In addition, the functions of the aforementioned embodiments are implemented by a computer executing the read-out program. It goes without saying that the present invention also includes the case where, for example, the OS (operating system) running on the computer performs part or all of the actual processing based on the instructions of the program, and the above-described embodiments are implemented by that processing.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-121644, filed May 7, 2008, which is hereby incorporated by reference herein in its entirety.

What is claimed is:

1. An X-ray radioscopy device comprising:
    an image capturing unit configured to capture images of an object that has been irradiated by X-rays, and generate multiple frames of image data;
    an analysis processing unit configured to perform different analysis processes in parallel on the image data in order to extract a plurality of specific regions of the object in the image data, wherein a first process of the analysis processes is faster than a second process of the analysis processes;
    a detection unit configured to detect a movement of the object in the multiple frames; and
    a selection unit configured to select a region from one of a specific region extracted in the first process and a specific region extracted in the second process based on the detected movement.

2. The X-ray radioscopy device according to claim 1, wherein the images are moving images including a plurality of frames.

3. The X-ray radioscopy device according to claim 1, wherein the region is a region of interest.

4. The X-ray radioscopy device according to claim 1, further comprising:
    a feature amount calculation unit configured to calculate a feature amount of the region selected by said selection unit;
    an image processing unit configured to perform image processing on a corresponding frame using the feature amount; and
    a display unit configured to display the result of the image processing.

5. The X-ray radioscopy device according to claim 4, further comprising an X-ray control unit configured to control an X-ray generation unit based on the feature amount calculated by said feature amount calculation unit.

6. The X-ray radioscopy device according to claim 1, wherein said analysis processing unit extracts the plurality of specific regions of the object from a frame to be processed using at least one of histogram analysis, edge detection through spatial filtering, a Hough transform, morphology computation, and pattern matching.

7. The X-ray radioscopy device according to claim 1, wherein said selection unit selects the region using at least one of the edge strength, edge length, edge luminance, and edge position of the region of interest extraction result, the luminance of the region of interest, the form of the region of interest, the central position of the region of interest, the average luminance value of the region of interest, and the variance value of the region of interest.

8. The X-ray radioscopy device according to claim 4, wherein said feature amount calculation unit calculates, based on the selected region, a feature amount expressing at least one of the position, size, form, average luminance value, maximum luminance value, minimum luminance value, central position, variance, and standard deviation of the region.

9. The X-ray radioscopy device according to claim 4, wherein said image processing unit performs, based on the feature amount, at least one of tone conversion processing, sharpening processing, noise suppression processing, and region of interest cutout processing as the image processing.

10. A moving image processing method for processing images of an object that has been irradiated by X-rays, the method comprising:
    an analysis processing step of performing different analysis processes in parallel on image data generated from images in order to extract a plurality of specific regions of the object in the image data, wherein a first process of the analysis processes is faster than a second process of the analysis processes;
    a detection step of detecting a movement of the object in multiple frames of the image data; and
    a selection step of selecting a region from one of a specific region extracted in the first process and a specific region extracted in the second process based on the detected movement.

11. The moving image processing method according to claim 10, wherein the images are moving images including a plurality of frames.

12. The moving image processing method according to claim 10, wherein the region is a region of interest.

13. The moving image processing method according to claim 10, further comprising:
    a feature amount calculation step of calculating a feature amount of the region selected in said selection step;
    an image processing step of performing image processing on a corresponding frame using the feature amount; and
    a display step of displaying the result of the image processing.

14. The moving image processing method according to claim 13, further comprising an X-ray control step of controlling an X-ray generation unit based on the feature amount calculated in said feature amount calculation step.

15. The moving image processing method according to claim 10, wherein said analysis processing step includes extracting the plurality of specific regions of the object from a frame to be processed using at least one of histogram analysis, edge detection through spatial filtering, a Hough transform, morphology computation, and pattern matching.

16. The moving image processing method according to claim 10, wherein said selection step includes selecting the region using at least one of the edge strength, edge length, edge luminance, and edge position of the region of interest extraction result, the luminance of the region of interest, the form of the region of interest, the central position of the region of interest, the average luminance value of the region of interest, and the variance value of the region of interest.

17. The moving image processing method according to claim 13, wherein said feature amount calculation step includes calculating, based on the selected region of interest, a feature amount expressing at least one of the position, size, form, average luminance value, maximum luminance value, minimum luminance value, central position, variance, and standard deviation of the region.

18. The moving image processing method according to claim 13, wherein said image processing step includes performing, based on the feature amount, at least one of tone conversion processing, sharpening processing, noise suppression processing, and region of interest cutout processing as the image processing.

19. A non-transitory computer-readable storage medium storing an image forming program which causes a computer to execute a moving image processing method for processing images of an object that has been irradiated by X-rays, the method comprising:
- an analysis processing step of performing different analysis processes in parallel on image data generated from images in order to extract a plurality of specific regions of the object in the image data, wherein a first process of the analysis processes is faster than a second process of the analysis processes;
- a detection step of detecting a movement of the object in multiple frames of the image data; and
- a selection step of selecting a region from one of a specific region extracted in the first process and a specific region extracted in the second process based on the detected movement.

20. An X-ray radioscopy device comprising:
- an image capturing unit configured to capture images of an object that has been irradiated by X-rays, and generate multiple frames of moving image data;
- an analysis processing unit configured to perform a first analysis processing and a second analysis processing in parallel on the moving image data in order to extract a plurality of specific regions of the object in the moving image data, wherein the first analysis processing is faster than the second analysis processing, wherein frames of the moving image data to be processed by the second analysis processing include at least one frame that differs from frames of the moving image data to be processed by the first analysis processing;
- a detection unit configured to detect a movement of the object in the multiple frames; and
- a selection unit configured to select a region from a specific region extracted in the first analysis processing and a specific region extracted in the second analysis processing based on the detection movement.

21. A moving image processing method for processing images of an object that has been irradiated by X-rays, the method comprising:
- an analysis processing step of performing a first analysis processing and a second analysis processing in parallel on moving image data generated from images and in order to extract a plurality of specific regions of the object in the moving image data, wherein the first analysis processing is faster than second analysis processing, wherein frames of the moving image data to be processed by the second analysis processing include at least one frame that differs from frames of the moving image data to be processed by the first analysis processing;
- a detection step of detecting a movement of the object in multiple frames of the moving image data; and
- a selection step of selecting a region from one of a specific region extracted in the first analysis processing and a specific region extracted in the second analysis processing based on the detection movement.

22. A non-transitory computer-readable storage medium storing an image forming program which causes a computer to execute a moving image processing method for processing images of an object that has been irradiated by X-rays, the method comprising:
- an analysis processing step of performing a first analysis processing and a second analysis processing in parallel on moving image data generated from images in order to extract a plurality of specific regions of the object in the moving image data, wherein the first analysis processing is faster than second analysis processing, wherein frames of the moving image data to be processed by the second analysis processing include at least one frame that differs from frames of the moving image data to be processed by the first analysis processing;
- a detection step of detecting a movement of the object in multiple frames of the moving image data; and
- a selection step of selecting a region from one of a specific region extracted in the first analysis processing and a specific region extracted in the second analysis processing based on the detected movement.

23. An X-ray radioscopy device comprising:
- an image capturing unit configured to capture images of an object that has been irradiated by X-rays, and generate multiple frames of image data;
- an analysis processing unit configured to perform different analysis processes in parallel on the image data in order to extract a plurality of specific regions of the object in the image data, wherein a first process of the analysis processes is faster than a second process of the analysis processes;
- an obtaining unit configured to obtain a value based on each of the extracted specific regions; and
- a selection unit configured to select a region from the extracted specific regions based on detected movement of the object in the multiple frames, by comparing obtained values of the extracted regions.

24. A moving image processing method of an X-ray radioscopy device comprising, the method comprising:
- an image capturing step of capturing images of an object that has been irradiated by X-rays, and generating multiple frames of image data;
- an analysis processing step of performing different analysis processes in parallel on the image data in order to extract a plurality of specific regions of the object in the image data, wherein a first process of the analysis processes is faster than a second process of the analysis processes;
- an obtaining step of obtaining a value based on each of the extracted specific regions; and
- a selection step of selecting a region from the extracted specific regions based on detected movement of the object in the multiple frames, by comparing obtained values of the extracted regions.

25. A non-transitory computer-readable storage medium storing an image forming program which causes a computer to execute a moving image processing method, the method comprising:
- an image capturing step of capturing images of an object that has been irradiated by X-rays, and generating multiple frames of image data;
- an analysis processing step of performing different analysis processes in parallel on the image data in order to extract a plurality of specific regions of the object in the image data, wherein a first process of the analysis processes is faster than a second process of the analysis processes;
- an obtaining step of obtaining a value based on each of the extracted specific regions; and
- a selection step of selecting a region from the extracted specific regions based on detected movement of the object in the multiple frames, by comparing obtained values of the extracted regions.

* * * * *